United States Patent
Covens et al.

(10) Patent No.: US 11,371,959 B2
(45) Date of Patent: Jun. 28, 2022

(54) ASSAY WITH DIGITAL READOUT

(71) Applicant: IMEC VZW, Leuven (BE)

(72) Inventors: Kris Covens, Hofstade (BE); Karolien Jans, Tessenderlo (BE); Koen Martens, Ghent (BE)

(73) Assignee: IMEC VZW, Leuven (BE)

( * ) Notice: Subject to any disclaimer, the term of this patent is extended or adjusted under 35 U.S.C. 154(b) by 205 days.

(21) Appl. No.: 16/715,541

(22) Filed: Dec. 16, 2019

(65) Prior Publication Data
US 2020/0191745 A1   Jun. 18, 2020

(30) Foreign Application Priority Data
Dec. 17, 2018   (EP) .................................. 18213099

(51) Int. Cl.
*G01N 27/414* (2006.01)
*G01N 27/413* (2006.01)
*G01N 27/416* (2006.01)

(52) U.S. Cl.
CPC ....... *G01N 27/4145* (2013.01); *G01N 27/413* (2013.01); *G01N 27/4167* (2013.01)

(58) Field of Classification Search
None
See application file for complete search history.

(56) References Cited

U.S. PATENT DOCUMENTS

| 2009/0026082 A1 | 1/2009 | Rothberg et al. |
| 2011/0195852 A1 | 8/2011 | Walt et al. |
| 2011/0263463 A1 | 10/2011 | Rothberg et al. |
| 2013/0204107 A1 | 8/2013 | Lee et al. |

OTHER PUBLICATIONS

Technical Guide for ELISA, SeraCare Life Science, KPL, Inc., 44 page, obtained Sep. 21, 2021 from https://www.seracare.com/globalassets/seracare-resources/tgprotocols-and-troubleshooting.pdf (Year: 2013).*
European Search Report, European Patent Application No. 18213099.7, dated Jun. 5, 2019, 10 pages.
Takehara, Hironari et al., "Compact Lensless Fluorescence Counting System for Single Molecular Assay", IEEE Transactions on Biomedical Circuits and Systems, vol. 12, No. 5, Oct. 2018, pp. 1177-1185.

(Continued)

*Primary Examiner* — J. Christopher Ball
(74) *Attorney, Agent, or Firm* — McDonnell Boehnen Hulbert & Berghoff LLP

(57) ABSTRACT

A device and a method for performing an assay is provided. The assay device, which may be used for determining the concentration of an analyte in a sample, includes a plurality of microchambers and a Field-effect transistor (FET) arranged at the bottom of each of the plurality of microchambers. Capture probe molecules for the analyte can be arranged within the plurality of microchambers such that each microchamber contains at most one capture probe molecule. The FET can be arranged in said microchamber to give a readable output signal based on binding of the analyte, or competitor to the analyte, with the capture probe molecule.

15 Claims, 4 Drawing Sheets

(56) References Cited

OTHER PUBLICATIONS

Whitepaper 1.0, "Scientific Principle of Simoa (Single Molecular Array) Technology", Jan. 1, 2013, retrieed from Internet: URL:http://www.healthtech.com/uploadedFiles/Conferences/White_Papers/MXA/Scientific-Principles-of-Simo-Technology.pdf, pp. 1-2.

De Moraes, Ana Carolina Mazarin et al., Recent Trends in Field-Effect Transistors-Based Immunosensors, Chemosensors, vol. 4, No. 20, 2016, pp. 1-26.

Choi, Kyungyong et al., "Integration of Field Effect Transistor-Based Biosensors With a Digital Microfluidic Device for a Lab-on-a-Chip Application", Lab Chip, vol. 12, 2012, pp. 1533-1539.

Im, Maesoon et al., "Development of a Point-of-Care Testing Platform With a Nanograp-Embedded Separated Double-Gate Field Effect Transistor Array and Its Readout System for Detection of Avian Influenza", IEEE Sensors Journal, vol. 11, No. 2, Feb. 2011, pp. 351-360.

Hong, Hyobong et al., "Label-Free and Real-Time Immunodetection of the Avian Influenza A Hemagglutinin Peptide Using a Silicon Field-Effect Transistor Fabricated by a Nickel Self-Aligned Silicide Process", Materials Transactions, vol. 53, No. 9, 2012, pp. 1633-1637.

Huang, Xiwei et al., "A Dual-Mode Large-Arrayed CMOS ISFET Sensor for Accurate and High-Throughput pH Sensing in Biomedical Diagnosis", IEEE Transactions on Biomedical Engineering, vol. 62, No. 9, Sep. 2015, pp. 2224-2233.

Hammock, Mallory L. et al., "Electronic Readout Enzyme-Linked Immunosorbent Assay With Organic Field-Effect Transistors as a Preeclampsia Prognostic", Advanced Materials, vol. 26, 2014, pp. 6138-6144.

Hammock, Mallory L. et al., "Electronic Readout Enzyme-Linked Immunosorbent Assay With Organic Field-Effect Transistors as a Preeclampsia Prognostic", Supporting Information, Advanced Materials, Copyright WILEY-VCH Verlag GmbH & Co., KGaA, 69469 Weinheim, Germany, 2014, 11 pages.

Kamahori, Masao et al., "Enzyme Immunoassay Using a Reusable Extended-Gate Field-Effect-Transistor Sensor With a Ferrocenylalkanethiol-Modified Gold Electrode", Analytical Sciences, vol. 24, Sep. 2008, pp. 1073-1079.

Basu, A.S., "Digital Assays Part I: Partitioning Statistics and Digital PCR", Micro- and Nanotechnologies for Quantitative Biology and Medicine, 2017, vol. 22(4), pp. 369-386.

* cited by examiner

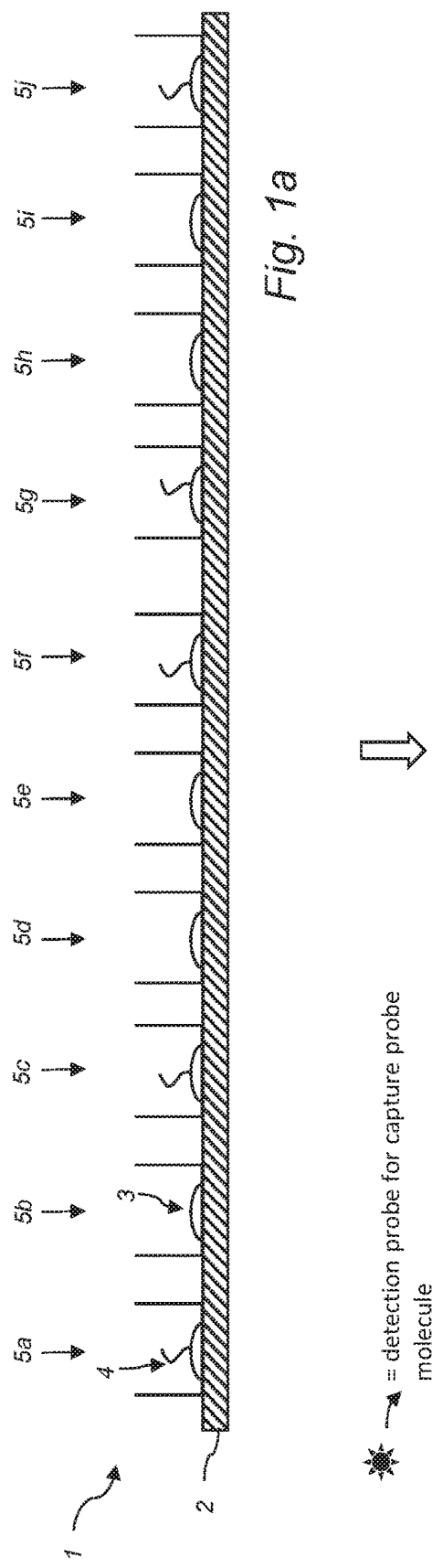
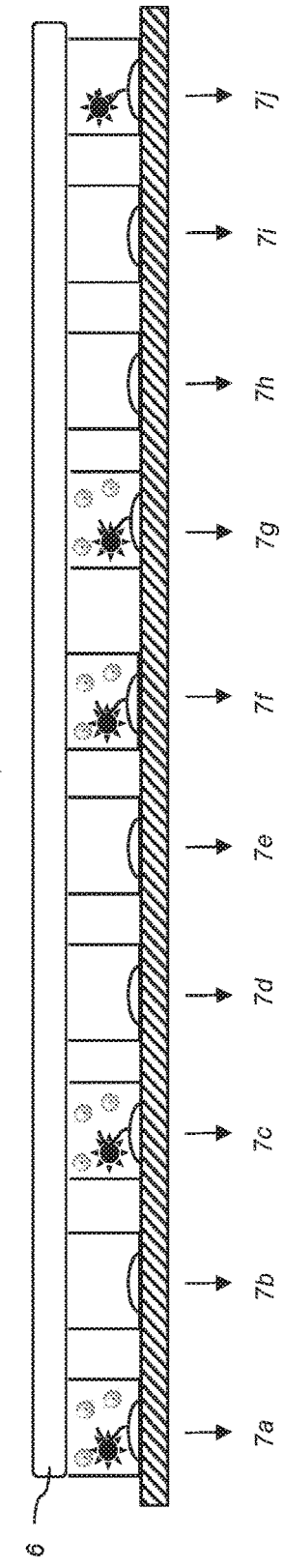

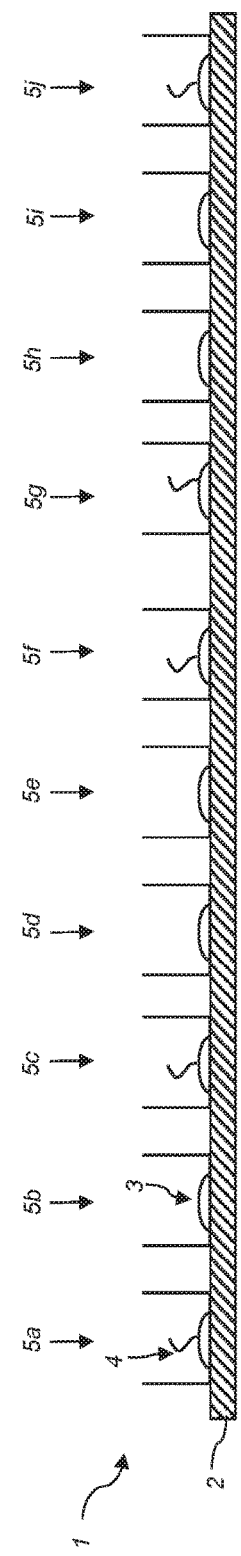
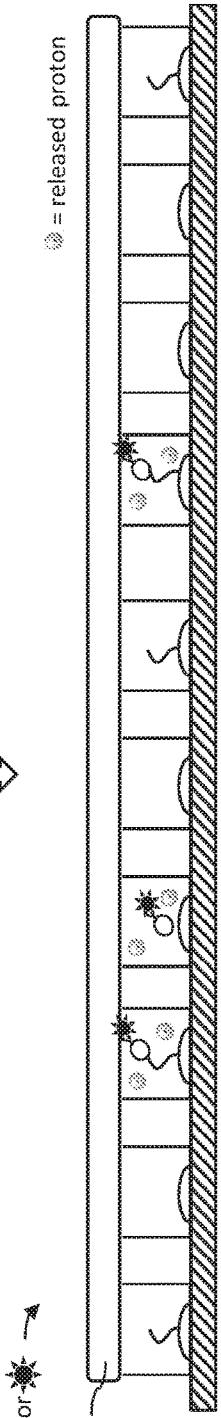
Fig. 2a
Fig. 2b
Fig. 2c

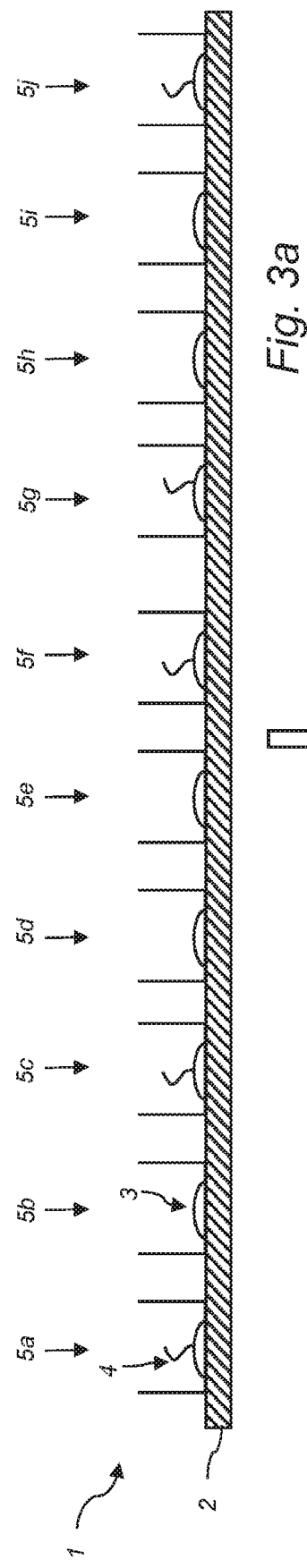
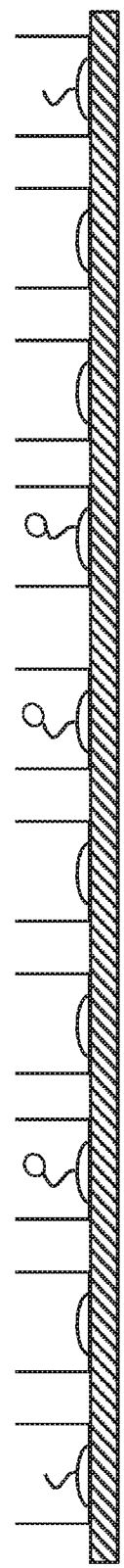
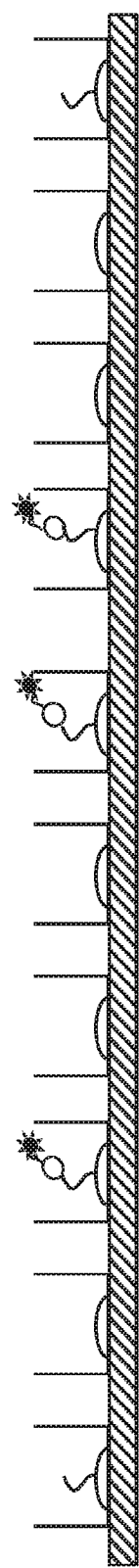
Fig. 3a
Fig. 3b
Fig. 3c

ASSAY WITH DIGITAL READOUT

CROSS-REFERENCE TO RELATED APPLICATIONS

The present application is a non-provisional patent application claiming priority to European Patent Application No. 18213099.7, filed Dec. 17, 2018, the contents of which are hereby incorporated by reference in its entirety.

FIELD OF THE DISCLOSURE

The present disclosure relates to an assay, such as an immunoassay, for determining the concentration of an analyte in a sample.

In particular, the present disclosure relates to an assay having a digital readout.

BACKGROUND OF THE DISCLOSURE

An immunoassay is a generic term to describe a range of different methods using affinity reagents that allows for the determination of the concentration of specific analytes (e.g. biomarkers predictive of certain diseases) circulating in body fluids (e.g. blood, plasma, urine) or in specimen used in research (e.g. cell culture medium). In an enzyme-linked immunosorbent assay (ELISA), the sample with the analyte of interest can be supplied to a surface and the analyte can bind to a capture probe for the analyte present on the surface. As an example, a specific antibody linked to an enzyme may then be used for binding to the captured analyte and after supply of the enzyme's substrate, a detectable signal is generated. This signal is often involves a colour change of the substrate of the enzyme. The generated signal per unit time can be correlated to the amount of bound analyte of interest, which in turn can correlate to the concentration in the sample. The relation between amount of bound analyte and the concentration in the sample is governed by the association rate constant of the interaction.

This association rate constant is empirically determined for each individual reaction in order to be able to predict the number of binding events to the capture probe per unit of time as a function of the analyte concentration. The number of binding events that are present at a given time after the initiation of the immunoassay will thus differ for each analyte under investigation, even when using different capture probes for the same analyte. In addition, the association rate can be dependent on environmental factors such as temperature. For instance, higher temperature can lead to more molecular motion. To allow the use of this type of immunoassays for analytes present at a low concentration, a very sensitive readout methodology is needed as well as knowledge of the characteristics of the binding partners.

However, there are thus a number of problems associated with using a sandwich immunoassay for low concentration analytes, such as the need for a very sensitive, high signal to background readout method, the empirical determination of the binding rate and tight control of reaction conditions.

An alternative way of performing an immunoassay is the so-called competitive immunoassay. In this case, labelled analyte itself as opposed to an affinity probe binding to the analyte in question can be added to the reaction mixture. As the labelled analyte can bind to the same receptor, decreased detection of the label (enzymatic, fluorescence, gold particle) is indicative of increased presence of the analyte itself in the test sample, when approaching the endpoint of the reaction. Since the total concentration of the analyte (i.e. the analyte itself and the added labelled competitor analyte) can be very large, the time to reach the endpoint of the reaction can be dramatically reduced and fine-tuned by adding more of the labelled competitor analyte. In addition, one can set a lower limit of time for the reaction to occur such that endpoint will be reached regardless of the exact temperature (or at least within a certain range of reasonable temperatures).

As such, a couple of problems related to the common sandwich immunoassay can be circumvented by a competitive immunoassay. Further, the need for controlling reaction conditions is less stringent. However, in a standard competitive immunoassay approach, using very high concentrations of labelled analyte can result in the problem that there is hardly any difference in signal when there is very low concentration of unlabelled analyte present. As a result, it can be difficult to detect analytes present at low concentrations when using standard methods.

There is thus a need in the art for improved assays, especially assays for determining the analyte concentrations in samples having a very low concentration of analyte.

SUMMARY OF THE DISCLOSURE

It is an object of the disclosure to at least partly overcome one or more limitations of the prior art. In particular, it is an object to provide improved assays for determining low analyte concentrations.

As a first aspect of the disclosure, an assay device is provided for determining the concentration of an analyte in a sample. The assay device comprises:
  a plurality of microchambers; and
  a Field-effect transistor (FET) arranged at the bottom of each of the plurality of microchambers, wherein capture probe molecules for said analyte are arranged within said plurality of microchambers such that each microchamber contains at most one capture probe molecule, and wherein said FET is arranged in said microchamber to give a readable output signal based on binding of said analyte, or competitor to said analyte, with said capture probe molecule.

The assay device may further comprise a substrate layer 2 onto which the plurality of microchambers can be arranged. The assay device may further comprise a fluidic system for supplying and distributing the sample over the plurality of microchambers. The assay device may, for example, comprise a fluidic inlet for the sample as well as a fluidic outlet for withdrawing the sample after having been distributed over the microchambers. Such a fluid inlet may further be used for supply of washing reagents and substrates for enzymatic reactions within the microchambers. There may also be control means for controlling the supply and flow rate of the sample to and from the microchambers. The control means may comprise pumps and valves.

In embodiments of the first aspect, the assay device can be a microfluidic assay device. Thus, fluidic system for supplying and distributing the sample over the plurality of microchambers may be a microfluidic system.

The assay device may further comprise microchambers other than the plurality of microchambers. As an example, the assay device may comprise microchambers that comprises more than one capture probe molecule, such as at least two capture probe molecules. Thus, in embodiments, the plurality of microchambers form a sub-set of all microchambers of the assay device.

A microchamber may have any type of geometrical form, as long as there is accessibility for the sample to reach the capture probe molecule present in the microchamber. Thus, the microchamber may have a cylindrical form.

The plurality of microchambers may be arranged in an array.

A first aspect of the disclosure can be based on the insight that having an assay device with a plurality of microchambers and a number of capture probe molecules per microchamber that allows for subsequent partitioning statistical analysis of the binding events which can be desirable in that it facilitates a digital immunoassay. Thus, a sample of low concentration may be partitioned into the microchambers and each partition (microchamber) may be individually assayed using the FETs.

As a configuration of the first aspect of the disclosure, an assay device is provided for determining the concentration of an analyte in a sample, the assay device comprising
a plurality of microchambers; and
a Field-effect transistor (FET) arranged at the bottom of each of the plurality of microchambers, wherein capture probe molecules for said analyte are arranged within said plurality of microchambers such that the number of capture probe molecules per microchamber is low enough to allow for subsequent partitioning statistical analysis of binding events between analyte and capture probe molecule within the plurality of microchambers, and wherein said FET is arranged in said microchamber to give a readable output signal based on binding of said analyte, or competitor to said analyte, with said capture probe molecule.

According to embodiments, the plurality of microchambers comprises at least 100 microchambers, at least 1000 microchambers, at least 10,000 microchambers, at least 100,000 microchambers, at least 200,000 microchambers, or at least 500,000 microchambers.

A higher number of microchambers may be used for detecting a lower concentration of analyte in the assay. As an example, having at least 100,000 microchambers may allow for the detection of the analyte at sub-femtomolar levels. Further, having at least 1000 microchambers may allow for detection of analyte at the femtomolar level, using a sandwich assay.

Consequently, the assay device may be useful for determining the concentration of an analyte in a sample with a detection limit at the femtomolar level, such as at a detection limit that is below the femtomolar level.

The total number of capture probe molecules distributed or arranged within the plurality of microchambers may be less than the plurality of microchambers. Further, the total number of capture probe molecules may be such that at least 10%, at least 25%, or at least 50%, of the plurality of microchambers comprises a capture probe molecule. Further, the total number of capture probe molecules may be such that between 20-50%, between 25-45%, or between 30-40% of the plurality of microchambers comprises a capture probe molecule.

In embodiments, the plurality of microchambers comprises at least 100, as at least 1000, at least 10,000, or at least 100,000 capture probe molecules.

A FET can be further arranged at the bottom of each of the plurality of microchambers. The microchambers may thus have a bottom wall and sidewalls, and the FET can then arranged at the bottom wall.

The FET may thus have a liquid gate during operation.

In embodiments, the FET can instead be arranged to be in contact with any of the walls of the microchamber, so as to give a readable output signal based on binding of said analyte, or competitor to said analyte, with the capture probe molecule.

According to embodiments, the FET can be an ISFET, i.e. field-effect transistor with, instead of a metal or poly gate, a gate electrode formed by an electrolyte. The ISFET can have a gate electrode formed by an electrolyte whose voltage determines the conductivity of the ISFET.

As an example, the FET may be a FinFET. A Fin Field-effect transistor (FinFET) can be a metal oxide semiconductor field-effect transistor (MOSFET) built on a substrate, such as silicon. The gate may be placed on two, three, or four sides of the channel or wrapped around the channel, forming a double gate structure. The source/drain region of a FinFET may form fins on the substrate surface.

The FET may also be a nanowire FET, which can be a FET with a nanometer sized cross section. The liquid gate (partially) wraps around the nanowire channel.

The readable output signal from the FET may be a voltage or current. The value of this voltage or current may be dependent on an ion concentration of the surrounding solution. As an example, the value of the voltage or current may be dependent on the pH, i.e. the concentration of $H^+$ and $OH^-$ ions, of the surrounding solution. Other FETs or MOSFETs having a solid gate instead of a liquid gate may be arranged near each sensor FET to aid reading the signal.

Thus, all sensor FETs arranged at the bottom of the plurality of microchambers may be arranged to give readable output signal, but this signal may be different if a sample analyte has bound to the capture probe molecule or not. In other words, the FETs may be arranged to give a first readable output signal if the analyte, or competitor to the analyte, has bound to the capture probe molecule and a second readable output signal, distinguishable from the first, if no analyte, or competitor to the analyte, has bound to the capture probe molecule.

The plurality of microchamber further comprises a number of capture probe molecules per microchamber that can be low enough to allow for subsequent partitioning statistical analyses to be performed based after assaying each individual microchamber. The plurality of microchambers may comprise at most one, i.e. one or zero, capture probe molecule per microchamber. These molecules may be arranged onto the FET, such as on the bottom wall of each microchamber, or e.g. arranged on the walls other than the wall that is in contact with the FET, as long as the binding event with the capture probe molecule can be detected by the FET.

In embodiments, the capture probe molecule comprises at most one binding site for the analyte or competitor to the analyte. Having only one binding site facilitates performing subsequent partitioning statistics for determining the concentration of the analyte in the sample.

The capture probe molecule may be a receptor for the analyte and/or a receptor for a competitor of the analyte. The capture probe molecule may thus have affinity for the analyte in the sample, such as having specific affinity for the analyte. The capture probe molecule may be an antibody, an engineered antibody, a nanobody, or any type of antibody fragment with affinity for the analyte.

As an example, the capture probe molecule may be a scFV or a fAb fragment.

As another example, the capture probe molecule may be selected from the group consisting of nanobodies, affibodies, aptamers, somamers, and alphabodies. Such capture probe molecules may have only one binding site for the analyte or competitor to the analyte.

Furthermore, the capture probe molecule may be attached to a bead or a nanoparticle. The bead may then aid in the determination of the presence or absence of a capture probe molecule in a microchamber. As an example, the capture probe molecule may be attached to a magnetic bead, a metallic bead or a charged bead.

The capture probe molecule may be adapted to give a change in an ion concentration in the microchamber upon conversion of a detection substrate. As a complement, the capture probe molecule may be attached to a detection probe that can be adapted to give a change in an ion concentration in the microchamber upon conversion of a detection substrate. The ion concentration may be the concentration of $OH^-$ or $H^+$.

In embodiments, the capture probe molecule can be adapted to give a pH change in the microchamber upon conversion of a detection substrate, or the capture probe molecule can be attached to a detection probe that can be adapted to give a pH change in the microchamber upon conversion of a detection substrate, and wherein said pH change can be detectable by said FET.

This may allow for determining whether a capture probe molecule is present in the microchamber or not. As an example, the capture probe molecule may have an attached detection probe, such as an attached enzyme, that upon conversion of a substrate gives a change in the pH of the microchamber. The enzyme may for example be selected from glucose oxidase, urease, and HRP.

The detection probe, such as an enzyme, may be attached to the capture probe by means of a linker. This linker may be a cleavable linker. After detecting whether capture probe is present or not, the enzyme can be removed by cleaving the linker. With such a cleavable linker approach, the same enzyme can be used as for the detector reagent, making use of the same substrate. Making use of the same substrate and same enzyme can be convenient. A fewer number reagents would be required for the assay and less optimization of the pH generating enzyme, ISFET and cavity pH response and assay would be required.

As an alternative, an "anti-capture probe" molecule may be used for determining if a capture probe molecule is present in the microchamber or not. Such an "anti-capture probe" molecule may be enzymatically labelled and presence or absence of its enzyme's activity may be used for detecting an "anti-capture probe" molecule.

As a second aspect of the disclosure, a method is provided for performing an assay for determining the concentration of an analyte in a sample, said method comprising the steps of
a) providing an assay device according to the first aspect;
b) supplying said sample to said assay device;
c) analysing the output signals from said FETs to determine the number of true positives and/or true negatives, wherein the number of true positives are the number of microchambers in which a capture probe molecule is present and in which a binding event between capture probe molecule and analyte has occurred and wherein the number of true negatives are the number of microchambers in which a capture probe molecule is present and in which a binding event between capture probe molecule and analyte has not occurred; and
d) determining the concentration of said analyte in said sample based on the determination of step c).

Effects and features of this second aspect can be largely analogous to those described above in connection with the first aspect. Embodiments mentioned in relation to the first aspect are largely compatible with the second aspect.

The device and method according to the disclosure thus provide for performing a digital assay. The term digital refers to performing the assay with a partitioning step into multiple, small reactions in the plurality of microchambers, such that single analyte molecules can be detected in such microchambers. In these microchambers, an output signal can be generated by the FET when an analyte is present, e.g. due to a pH change generated by the conversion of a substrate by a detection probe, and no signal when the analyte is absent. Quantification in steps c) and d) can then be performed for example by counting the number of partitions that show presence of the analyte. Thus, the digital assay may rely on the production of a large number of microchambers, supplying and partitioning of a diluted analyte in the microchambers and reading the output from the individual partitions/microchambers.

Step d) may comprise determining the concentration of said analyte in said sample based on the determination of step c) and information on the total number of microchambers in which a capture probe molecule is present. As such, there may be no need for calibration curves to determine the concentration of the analyte in question. Instead, partitioning statistics may be used for determining the concentration of the analyte in the sample. In addition, digital immunoassays have greatly enhanced sensitivity when compared to regular immunoassays.

The method comprises counting the number of true positives and/or true negatives, wherein the number of true positives can be the number of microchambers in which a capture probe molecule is present and in which a binding event between capture probe molecule and analyte has occurred and wherein the number of true negatives can be the number of microchambers in which a capture probe molecule is present and in which a binding event between capture probe molecule and analyte has not occurred.

The analysis of step c) may further comprise determining the total number of microchambers in which a capture probe molecule is present. The method of step c) may thus comprise determining the number of true positive and/or the number of true negatives and further determining the total number of microchambers in which a capture probe molecule is present.

In addition, by considering microchambers in which no capture probe molecule was present but in which signal generation occurs, i.e. false positives, non-specific binding can be quantified. This applies to both competitive and sandwich immunoassays.

The device and method of the present disclosure allows for sample handling that can be less complex than conventional immunoassay. Such assays usually require high concentrations of capture and detector antibodies which in turn requires thorough washing etc. prior to dispensing any detector antibodies to the microchambers. However, the method of the present disclosure also may comprise steps of washing etc. between any of the steps a)-d).

In addition, the device and method may allow for standardization across immunoassays using different capture probes or even for different analytes. This is because the ratio of binding by labelled/unlabelled analytes may only be dependent on the ratio of these two and not on other properties of the antibodies. As such, the need for calibrator curves can be decreased and may in some cases be omitted. An immediate application can be the determination of the concentration of analytes present at low concentration in a fast way. Further applications of the device and method include determination of viral loads through immunoassays rather than through nucleic acid extraction and amplification, which can be a time-consuming method that requires highly trained personnel or complex, bulky and expensive automated laboratory equipment.

Other applications include detection of biomarkers present in a patient prior to the moment that certain disease patterns are diagnosed allowing true preventive medicine. Examples of this include biomarkers indicative of the later development of Alzheimer's disease or tumour biomarkers.

Partitioning of the sample into the multiple of microchambers provides for several benefits over traditional assay methods, such as it measures the contribution from individual molecules instead of an ensemble effect.

Thus, in embodiments of the second aspect, step d) comprises determining the concentration of said analyte in said sample by partitioning statistics using the number of true positives and/or true negatives.

Partitioning into the plurality of microchambers results in a statistical distribution of the analyte among the microchambers. The number of analytes in the sample may be less than, or in the order of, the number of microchambers. However, the number of analytes in the sample may also be higher than the number of microchambers.

The probability that a microchamber will be a true positive may be governed by binomial and Poisson distributions, as known in the art, and the concentration may be calculated e.g. using the fraction of empty microchambers, i.e. number of true negatives.

The analyte can be randomly distributed so the probability of the analyte being in close enough proximity to actually interact with the capture probe may also need to be taken into account. Such a probability will increase with incubation time.

For the sandwich assay, there may be a threshold analyte concentration that will, for certain assay parameters such as incubation time, cover all capture probes in the microchambers.

Using partitioning statistics allows for determination of the concentration without the need of a calibration curve. Accordingly step d) may comprise determining the concentration of said analyte in said sample without using a calibration curve.

Furthermore, the device and method of the disclosure may be used in sandwich assays, in which the analyte of interest can be labelled, such as labelled with a detection probe.

Thus, in embodiments, the output signals analysed in step c) may be triggered by a detector reagent bound to said analyte in said sample.

The detector reagent may for example be an enzymatic label bound directly to the analyte, or it may be attached to an affinity probe, such as an antibody, with affinity for the analyte. Thus, the analyte may for example be indirectly labelled using e.g. a detector reagent. The analyte may for example be detected with a first, unlabelled antibody. This first antibody may then be detected by a labelled secondary antibody.

The analyte may be labelled with the detector reagent prior to introducing the sample to the device. Thus, in embodiments, step b) comprises a step b1) of labelling said analytes with said detector reagent and a step b2) of supplying said labelled sample to said assay device.

However, as an alternative, the analyte may be labelled after supply to the device. Consequently, step b) may comprise supplying said detector reagent to said assay device after supplying said sample to said assay device. The detector reagent may be supplied after a step of washing said microchambers. The supplied detector reagent may be attached to an affinity probe, such as an antibody, that can be supplied after the sample has been supplied to the device.

When using the device and method in a classical sandwich assay, it may be enough to determine the number of true positives of the plurality of microchambers. Thus, in embodiments, step d) comprises determining the concentration of said analyte using the number of true positives only.

However, in a sandwich assay or a competitive assay, it may also be enough to determine the number of true negatives only. Consequently, in embodiments, step d) comprises determining the concentration of said analyte using the number of true negatives only.

This device and method of the present disclosure further provides performing a competitive assay. This may avoid issues of sandwich assay kinetics while solving the readout sensitivity issue typically observed in competitive assays. In a competitive assay, unlabelled analyte in the sample competes with labelled analyte, or labelled competitor, to bind to the capture probe molecule. It thus becomes possible to detect/count individual binding events e.g. by a labelled competitor analyte spiked in the sample before supply to the device. For quantification of the analyte present in the investigated sample, counting the microchambers that contain the detector probe molecule on the FET, but in which no signal is generated (true negatives) may allow for counting the number of microchambers in which an unlabelled analyte has bound. However, the number of true negatives may follow immediately when knowing the number of true positives, i.e. counting the number of true positives may be an option for determining the number of true negatives.

Thus, in embodiments, the output signals may be triggered by a detector reagent bound to a competitor for said analyte present in said sample.

Further, step b) may comprise the step of adding a labelled competitor for said analyte to said sample. The labelled competitor may be a labelled analyte. Thus, a known concentration of labelled analyte may be added to the sample before performing the assay.

When performing a competitive assay, step d) may comprise determining the concentration of said analyte using the ratio of true positives to true negatives for a given concentration of said competitor for said analyte.

In order to get a detectable signal from the detector reagent, a substrate may need to be added. The substrate may thus be an enzyme substrate in the case where the detector probe is an enzyme.

Consequently, in embodiments, the method can further comprise a step of supplying a substrate to said detector reagent, wherein the detector reagent and said substrate have the capacity to give a pH change in said microchamber upon conversion of said substrate by said detector reagent, thereby triggering said output signal in said FET.

As an example, the substrate may be D-glucose if the detector reagent is glucose oxidase. Conversion of D-glucose by glucose oxidase results in a proton release, that affects the pH of the microchamber which in turn affect the FET to give a readable output signal.

Moreover, the presence or absence of the capture probe molecule in the plurality of microchambers may be detected on each individual FET prior to performing the immunoassay.

Thus, in embodiments, the method can further comprise a step of determining the absence or presence of a capture probe molecule in each microchamber by analysing output signal from said FETs.

Detection of the actual capture probe molecules in the chambers may be performed in the same way as detecting the presence of bound analyte in the chamber.

As an example, step a) may further comprise the steps of
a1) supplying a detection probe for said capture probe molecule to said assay, and
a2) supplying a substrate for said detection probe; wherein the detection probe and said substrate have the capacity to give a pH change in said microchamber upon conversion of said substrate by said detection probe, thereby triggering said output signal in said FET.

The detection probe used for detecting a capture probe molecule may be the same as a detector reagent used for detecting the presence of an analyte in the microchamber.

BRIEF DESCRIPTION OF THE DRAWINGS

The above, as well as additional objects and features of the present disclosed concept, will be better understood through the following illustrative and non-limiting detailed description, with reference to the appended drawings. In the drawings like reference numerals will be used for like elements unless stated otherwise.

FIGS. 1a-1c shows a representative assay device and determination in which microchamber a capture probe molecule is present. FIG. 1a illustrates a schematic assay device 1 for determining the concentration of an analyte in a sample according to the present disclosure. FIG. 1b illustrates a detection probe for an unlabelled capture probe molecule 4 can be supplied to the device so that it may bind to the capture probe molecules in the microchambers. The capture probe molecules with attached detection probes may in this way be adapted to give a pH change in the microchambers. FIG. 1c illustrates that the presence or absence of such a readout signal for each microchamber may be monitored as shown by arrows 7a-7i.

FIGS. 2a-2c show a schematic embodiment of a sandwich assay method using the assay device 1 of FIGS. 1a-1c. FIG. 2a shows a schematic embodiment of a sandwich assay method using the assay device 1. FIG. 2b shows a sample comprising the analyte of interest being supplied to the device 1. FIG. 2c shows that when analysing the output signals from the microchambers, and with information about in which microchambers a capture probe molecule is present, it may be possible to discriminate between different types of microchambers.

FIGS. 3a-3c show a further example of a representative assay device and a sandwich method. FIG. 3a show a representative assay device and sandwich method. FIG. 3b shows that the analyte is unlabelled when supplied to the assay device, and a detector reagent is, after the analyte in the sample has been allowed to bind to the capture probe molecule, subsequently supplied to the assay device to allow binding of detector reagent to analyte. The detector reagent may for example be an antibody with affinity to the analyte. FIG. 3c show a representative assay device and sandwich method.

FIGS. 4a and 4b thus each show an example of a competitive assay in which the competitor may be supplied to the assay device concurrently with the sample.

DETAILED DESCRIPTION OF THE DISCLOSURE

Figure 4A:
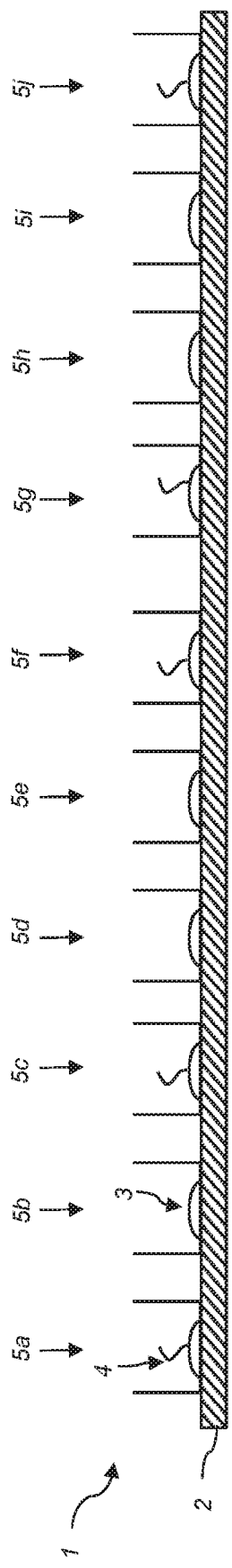
FIGS. 4a and 4b illustrate an embodiment in which a competitor labelled with a detector reagent may be mixed with the sample prior to supplying the sample to the assay device.

Detailed embodiments of the present disclosure will now be described with reference to the drawings.

The above disclosed concept has mainly been described with reference to a limited number of examples. However, as is readily appreciated by a person skilled in the art, other examples than the ones disclosed above are equally possible within the scope of the inventive concept, as defined by the appended claims.

The present disclosure is related to measuring concentrations in of analytes in so-called digital assays, such as immunoassays.

A schematic assay device 1 for determining the concentration of an analyte in a sample according to the present disclosure is shown in FIG. 1a. The device 1 can comprise a substrate 2, such onto which a plurality of microchambers 5a-5i can be arranged. The microchambers may be arranged in an array and the plurality of microchambers may be at least 100, at least 1000, at least 10,000, at least 100,000, at least 200,000, or at least 500,000 microchambers.

Arranged at the bottom of each well is a Field-effect transistor (FET), in this case a FinFET 3. Further, in the plurality of microchambers 5a-5i, either none or a single capture probe molecule 4 can be arranged. In the schematic example of FIG. 1a, microchambers 5a, 5c, 5f, 5g and 5j has a single capture probe molecule 4, whereas microchambers 5b, 5d, 5e, 5h and 5i has no capture probe molecule 4. The capture probe molecules 4 in this example may be attached to the outer surface of the FinFETs 3.

The capture probe molecules may be arranged within the plurality of microchambers in an amount of capture probe per microchamber that allows for subsequent analysis of the binding events in the microchambers by the use of partitioning statistical analysis. As an example less than three, such as less than two such as at most 1 capture probe molecule may be present in a microchamber.

Further, the number of microchambers being occupied with a capture probe molecule may be at least 10%, such as between 30-40%.

A higher total number of microchambers allow for a lower number of microchambers being occupied with a capture probe molecule but still give enough reading points. The number of microchambers being occupied with a capture probe molecule may also be dependent on the actual concentration range of the analyte you want to measure.

The assay device 1 further comprises a fluidic inlet (not shown), a fluidic outlet (not shown) as well as fluidics (not shown) for distributing a sample supplied to the fluidic inlet over the plurality of microchambers 5a-5i. The fluidic outlet may thus be used for discharging sample from the device 1.

Furthermore, the FinFETs may be arranged to give a readable output signal based on binding of an analyte, or competitor to the analyte, with said capture probe molecule 4.

In this example, the capture probe molecules 4 may be adapted to give a pH change in the microchamber 5a-5i upon conversion of a detection substrate, wherein said pH change can be detectable by said FET. This is illustrated in FIGS. 1b and 1c. In FIG. 1b, a detection probe for an unlabelled capture probe molecule 4 can be supplied to the device so that it may bind to the capture probe molecules in the microchambers. The capture probe molecules with attached detection probes may in this way be adapted to give pH change in the microchambers. Thus, after washing, a substrate for the detection probe may be supplied to the device 1. An oil seal 6 may be added to the device to allow for sealing the individual microchambers. However, other types of seals may also be used for sealing the individual microchambers. Upon conversion of the substrate by the detection probes, protons may be released. This release leads to a pH change within the microchamber, which in turn yield a readable output signal from the FinFET. As an alternative, hydroxyl ions or other ions may be released by conversion of the substrate, and this change in ion concentration may yield a readable output signal. Another alternative, an enzyme that consumes a proton or a hydroxyl ion upon conversion of a substrate can be used, since such an enzyme can also yield a pH change that could be measurable.

The presence or absence of such a readout signal for each microchamber may be monitored, as illustrated by arrows 7a-7i in FIG. 1c.

Consequently, different methodologies may be used to determine if a capture probe molecule, such as a receptor, is present in a microchamber, for example:
  i) having an enzyme attached to the capture probe molecule covalently and measure its activity (using pH changes as described above);
  ii) determining the presence of capture probes molecules (e.g. IgG) by incubating them with an enzymatically labelled anti-receptor probe (e.g. HRP-labelled IgG), determine presence/absence of the capture probe by measuring pH changes (as described above);
  iii) determining the presence of capture probes molecules by incubating the microchambers with magnetic, metallic, or dielectric beads with affinity for the capture probe molecule The presence or absence of such a bead may be detected by conventional means. As an alternative, a magnetic, metallic, or dielectric bead may be coupled to the capture probe molecule before it is immobilized in the microchambers.

FIGS. 2a-2c show a schematic embodiment of a sandwich assay using the assay device 1 of FIGS. 1a-1c. In FIG. 2b, the sample comprising the analyte of interest may be supplied to the device 1. In this example, the analyte has previously been labelled with a detector reagent, such as an enzyme. This leads to binding of the analyte in microchambers. After washing, a substrate for the detector reagent may be added. Addition of oil may also create an oil seal so that the reaction between capture probe and substrate may continue undisturbed. The substrate turnover by the detector reagent leads to the release of protons and thus a pH change in the microchambers. When analysing the output signals from the microchambers, and with information about in which microchambers a capture probe molecule is present, it may be possible to discriminate between microchambers of the following types, as also illustrated by FIG. 2c:

| | |
|---|---|
| true positives | microchambers in which a capture probe molecule is present and in which a binding event between capture probe molecule and analyte has occurred |
| true negatives | microchambers in which a capture probe molecule is present and in which a binding event between capture probe molecule and analyte has not occurred |
| false positives | microchambers in which a capture probe molecule is absent but still indicate that substrate turnover reaction has occurred in the microchamber when detecting the analyte |
| irrelevant | microchambers in which a capture probe molecule is absent and indicate that substrate turnover reaction has occurred in the microchamber |

In some embodiments, the false positives can be considered as irrelevant.

For a sandwich assay, it may be enough to count the number of true positives to be able to determine the analyte concentration. The number of true positives may this be regarded as "1" microchambers in the digital assay, whereas the number of true negatives may be regarded as "0" microchambers in the digital assay.

As an example, the examples shown in FIGS. 1a-1c and 2a-2c may give an experimental design as follows if a capture antibody is used as the capture probe molecule:
  1. Dilute sample in a dilution buffer that contains an enzyme-labelled detector reagent (or a labelled competitor for a competitive immunoassay). Ensure sufficient time for enzyme-labelled detector reagent to fully cover the analyte in question, which may be dependent on both reagent and concentration of the reagent;
  2. In parallel, or prior to adding the diluted sample to the assay device and the plurality of microchambers: determine in which microchambers a capture antibody is present;
  3. Remove reagents used to determine in which microchambers the capture antibody is present. This step may not be necessary if a magnetic bead is used for detection of the capture probe;
  4. Apply diluted sample to the assay device and the plurality of microchambers (incubation time may be dependent on specific assay);
  5. Wash away the sample and apply substrate for enzymatic reaction that generates a pH change the signal (pH change, see below);
  6. Seal of the top by applying oil, which may prevent that product of enzymatic reaction diffuses out of the microchambers;
  7. Determine in which well a pH change occurs (evidence of enzymatic reaction) by analysing readout from the FET in the microchamber.

As known from Basu, B: *Micro-and Nanotechnologies for Quantitative Biology and Medicine* (2107), vol 22(4), 369-386, a digital assay in which, e.g. 200,000. events are counted, a detection limit of below 0.5 femtomolar may be reached, whereas if e.g. 5000 partitions are counted, a detection limit of about 50 femtomolar may be obtained.

FIGS. 3a-3c show a further embodiment of the method of the present disclosure. The difference between this setup and the embodiment of FIGS. 1a-1c and FIGS. 2a-2c is that the analyte is unlabelled when supplied to the assay device (FIG. 3b), and a detector reagent is, after the analyte in the sample has been allowed to bind to the capture probe molecule, subsequently supplied to the assay device to allow binding of detector reagent to analyte. The detector reagent may for example be an antibody with affinity to the analyte.

When analysing the output signals from the microchambers, and with information about in which microchambers a capture probe molecule is present, it may be possible to discriminate between microchambers as discussed in relation to by FIG. 2c above.

Figure 4B:
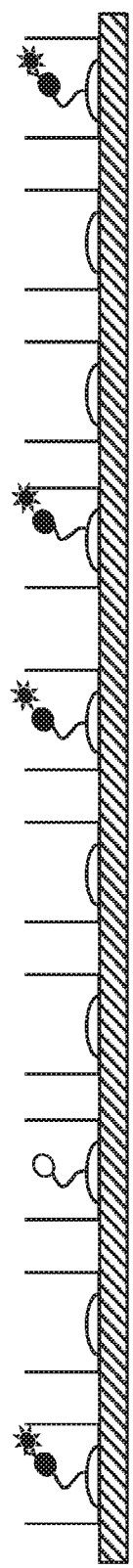

FIGS. 4a and 4b illustrate an embodiment in which a competitor labelled with a detector reagent may be mixed with the sample prior to supplying the sample to the assay device. FIGS. 4a and 4b thus show an example of a competitive assay in which the competitor may be supplied to the assay device concurrently with the sample. The concentration of the labelled competitor may be higher than the expected concentration of the analyte. However, the concentration of the labelled competitor may also be lower than the concentration of the analyte. The analyte and the competitor can compete for the binding with the capture probe molecule in the microchambers. Thus, the total concentration of analyte and labelled competitor can result in complete occupation of the capture probes under the reaction conditions, and thus result in competition for free capture probes between the analyte and labelled competitor when the reaction approaches endpoint.

After supply of a substrate for the detector reagent, an analysis of the readout signals from the FETs may thus give information on in which microchambers a competitor has bound. This may in turn be used for determining the concentration of the unlabelled analyte in the sample.

For competitive assay, the ratio of "1" microchambers to "0" microchambers (i.e. the ratio of true positives to true negatives), given known concentration of added competitor, may be used to deduct the concentration of unlabelled analyte in sample. This may be the case if the competitor and the analyte bind ratiometrically to the capture probe molecule. However, not only the ratio of true positives to true negatives may be used, but as an alternative only the number of true positives or true negatives, as well as the total number of microchamber with a capture probe can be used to deduct the concentration of unlabelled analyte in sample.

When analysing the output signals from the microchambers, and with information about in which microchambers a capture probe molecule is present, it may be possible to discriminate between microchambers as discussed in relation to by FIG. 2c above.

Signal Generation and Conversion:

As discussed above, a detectable readout signal in the microchamber may be generated by an enzymatic label. This enzymatic label may e.g. be on the capture probe molecule, on the sample analyte, on an antibody with affinity for the analyte, on a competitor for the analyte or on an antibody against such a competitor. Such an enzyme may convert a substrate that is specifically added to the assay device and upon conversion of the substrate ions such as protons (or in other cases hydroxyl ions) are released/consumed. A proton (/hydroxyl) release/consumption may result in a change of the pH in the microchamber where the enzyme is present and it is this pH change that may be measured by the FETs.

An example of proton-releasing reaction is the conversion of D-glucose by glucose oxidase (GOx) depicted below. This may be performed in the presence of $FeSO_4$ to induce the decomposition of $H_2O_2$, as such shifting the reaction towards the right side, resulting in enhanced proton release.

Further, an example of an enzyme that consumes hydroxyl ions is Urease.

An example of an enzyme that consumes protons in the conversion of a substrate is horseradish peroxidase (HRP), e.g. when converting 3,3',5,5'-Tetramethylbenzidine (TMB).

Analysing Readout Signal from FET

As discussed above, conversion of a substrate by e.g. an enzyme attached to a capture probe molecule or attached to a bound analyte, may lead to a change in ion concentration, such as a change in pH, in the microchamber. This change in concentration may for example be detected by the finFET in the microchamber, due to the finFET having an electrolyte as a gate electrode and the sensitivity to pH is the result of protonation/deprotonation of surface groups (e.g. SiOH (silanol) in case of a $SiO_2$ surface).

The readable output signal from the FET may be a voltage or a current. Other FETs, MOSFETs, without a liquid but with a solid gate may be arranged in the neighbourhood of each sensor FET to aid reading out the signal.

Determination of Concentration

As discussed above, the concentration of the analyte in the sample may be determined from the true positives and/or true negatives using partitioning statistics. Below follow some explicit examples on this may be achieved.

Sandwich Immunoassays

At low concentrations, the number of microchambers in which a binding event with the capture probe molecule has occurred, i.e. true positives, may be smaller than the total number of capture probe molecules in the microchambers.

For example, 100 µl of a 1 femtomolar solution contains ~60,000 analyte molecules, so if there are >>60,000 microchambers with a FET that contain a capture probe molecule, the Poisson distribution can be used to describe the probability of a microchamber being a true positive or a true negative ("1" microchamber or a "0" microchamber). The Poisson distribution describes the likelihood of a number of possible events occurring if the average number of events is known. If the expected average number of occurrences is, then the probability that there are exactly v occurrences is given by (Poisson)

$$P_\mu(v) = e^{-\mu}\left(\frac{\mu^v}{v!}\right)$$

In a digital assay, the key variable in this equation (µ) may be equal to the ratio of captured and labelled analyte molecules to the FETs in the microchambers. If we name $P_\mu(0)$ or the fraction of "true negative" microchambers, then $$\mu = -\ln[P_\mu(0)]$$

Since the fraction of "true negative" may be equal to one minus the fraction of "true positive" microchambers, it is possible to determine µ or the from $f_{on}$ (the fraction of "true positive" microchambers) using $$\mu = -\ln[1-f_{on}]$$

Since can be determined, the number of occurrences may be determined.

Reagent-specific parameters ($k_{on}$ and $k_{off}$ of the reagents) may determine the relation between the analyte concentration and the number of true positive microchambers.

In addition, non-specific binding may lead to assay (reagent, incubation time, buffer and temperature) specific background levels. Thus the background limit may be different for each assay (and assay comprises reagents, buffer conditions etc.). It may therefore be beneficial in some applications carry out the assay with samples containing known concentrations of the analyte to determine the number of true positive microchambers.

Consequently, in embodiments of the present disclosure, the method may also comprise a step e1) of supplying samples containing known concentrations of the analyte to said device; and a step e2) of analysing the output signals from the FETs to determine the number of true positives and/or true negatives of the samples supplied in step e1).

Further, the method may comprise using the determination from step e2) to create a calibration curve for the analyte.

Competitive Immunoassays

In competitive immunoassays, the conversion of the number of true positive microchambers to the concentration of analyte may be dependent on assay specific parameters, i.e. the concentration of labelled competitor.

In addition, also for this case non-specific binding may occur. Thus, also when performing a competitive digital assay samples containing known concentrations of the analyte in question may be used to determine the number of true positive microchamber. The determination may then be used for making calibration curves for the analyte.

The invention claimed is:

1. A method for performing an assay for determining a concentration of an analyte in a sample, the method comprising the steps of a) providing an assay device comprising:
a plurality of microchambers;
a Field-effect transistor (FET) arranged at the bottom of each microchamber of the plurality of microchambers; and
capture probe molecules for the analyte arranged within the plurality of microchambers such that each microchamber in the plurality of microchambers contains at most one capture probe molecule,
wherein the FET is arranged in the microchamber to give a readable output signal based on binding of said analyte, or a competitor to the analyte, with the capture probe molecule;
b) supplying the sample to the assay device;
c) analysing the output signals from the FETs to determine a number of true positives and/or true negatives, wherein the number of true positives is a number of microchambers in which the capture probe molecule is present and in which a binding event between the capture probe molecule and the analyte has occurred and wherein the number of true negatives is a number of microchambers in which the capture probe molecule is present and in which a binding event between the capture probe molecule and the analyte has not occurred; and
d) determining the concentration of the analyte in the sample based on the determination of step c).

2. The method according to claim 1, wherein step d) comprises determining the concentration of the analyte in the sample by partitioning statistics using the number of true positives and/or true negatives.

3. The method according to claim 2, wherein step d) comprises determining the concentration of the analyte in the sample without using a calibration curve.

4. The method according to claim 1, wherein the output signals analysed in step c) are triggered by a detector reagent bound to the analyte in the sample.

5. The method according to claim 4, wherein step b) comprises a step b1) of labelling the analyte with the detector reagent and a step b2) of supplying the labelled analyte in the sample to the assay device.

6. The method according to claim 4, wherein step b) comprises supplying the detector reagent to the assay device after supplying the sample to the assay device.

7. The method according to claim 4, wherein step d) comprises determining the concentration of the analyte using the number of true positives only.

8. The method according to claim 1, wherein the output signals are triggered by a detector reagent bound to a competitor for the analyte present in the sample.

9. The method according to claim 8, wherein step d) comprises determining the concentration of the analyte using the ratio of true positives to true negatives for a given concentration of the competitor for the analyte.

10. The method according to claim 4, further comprising a step of supplying a substrate to the detector reagent, wherein the detector reagent and the substrate have the capacity to give a pH change in the microchamber upon conversion of the substrate by the detector reagent, thereby triggering the output signal in the FET.

11. The method according to claim 1, further comprising a step of determining the absence or presence of a capture probe molecule in each microchamber by analysing the output signals from the FETs.

12. The method according to claim 1, wherein the plurality of microchambers comprises at least 100, at least 1000, at least 10,000, or at least 100,000 microchambers.

13. The method according to claim 1, wherein the plurality of microchambers comprises at least 1000, at least 10,000, or at least 100,000 of the capture probe molecules.

14. The method according to claim 1, wherein the capture probe molecule is adapted to give a pH change in the microchamber upon conversion of a detection substrate, and wherein the pH change is detectable by said FET.

15. The method according to claim 1, wherein the capture probe molecule is attached to a detection probe that is adapted to give a pH change in the microchamber upon conversion of a detection substrate, and wherein the pH change is detectable by said FET.

* * * * *